United States Patent [19]
Kumada et al.

[11] Patent Number: 4,928,502
[45] Date of Patent: May 29, 1990

[54] EQUIPMENT FOR STORING BLOOD

[75] Inventors: Susumu Kumada; Mikio Mori; Ryoji Nagatani; Tadami Ano, all of Nagasaki, Japan

[73] Assignee: Mitsubishi Denki Kabushiki Kaisha, Tokyo, Japan

[21] Appl. No.: 386,116

[22] Filed: Jul. 28, 1989

[30] Foreign Application Priority Data

Aug. 26, 1988 [JP] Japan ................ 63-213210

[51] Int. Cl.$^5$ .............................. F25D 11/00
[52] U.S. Cl. ............................ 62/440; 62/6; 62/78; 62/457.9
[58] Field of Search ............ 62/60, 78, 6, 457.9, 62/440

[56] References Cited

U.S. PATENT DOCUMENTS 3,163,994 1/1965 Haumann et al. ............ 62/457.9
4,827,736 5/1989 Miura et al. .................. 62/6

FOREIGN PATENT DOCUMENTS 54-41838 12/1979 Japan .
57-54692 11/1982 Japan .
62-33503 7/1987 Japan .

Primary Examiner—Ronald C. Capossela
Attorney, Agent, or Firm—Burns, Doane, Swecker & Mathis

[57] ABSTRACT

The equipment of the present invention has a plurality of storing cases in which the blood is stored and which is refrigerated by respectively provided Stirling refrigerator, in a keeping-cool room kept at a low temperature. According to the present invention, it is possible to obtain a very low temperature condition less than the recrystallization temperature of the ice in each of the storing cases, refrigerating each storing case wherein the blood is stored by each Stirling refrigerator with high performance coefficient in a very low temperature. A very low temperature condition is realized at a low cost and a high recovery is obtained, which results in that a great deal of blood is stored stably. Furthermore, taking blood in and out is carried out automatically and without the necessity of the operator's entering the keeping-cool room, by providing means for putting the blood in each storing case and taking it out from each storing case and performing the remote control of this means.

11 Claims, 7 Drawing Sheets

EQUIPMENT FOR STORING BLOOD

BACKGROUND OF THE INVENTION

1. Field of the Invention

The present invention relates to an equipment for storing blood, sorting out various kinds of and a great deal of blood.

2. Description of Related Art

In order to store blood stably over a long period, it is necessarry to freeze blood at a very low temperature less than $-135°$ C., that is, the recrystallization temperature of ice. As a device for storing a great deal of blood in such purpose for transfusion or the like, a Dewar bottle has conventionally been used, as shown in FIG. 1.

In FIG. 1, numeral 21 is an inner globe which is in a globular shape having an opening on a side and holds liquefied nitrogen 20 within. The inner globe 21 is supported in an outer globe 22 which is a little larger than it and of substantially a similar figure with it, by a plurality of supporting members 23 provided between both globes substantially concentrically therewith. A space 24 formed between the inner globe 21 and the outer globe 22 is kept at a high vacuum by the action of a low temperature absorbent 25 held in a space which is formed at the bottom of the inner space 21 and communicates with the space 24. The inner globe 21 and the outer globe 22 are supported in a housing 26 by a support spring 27 provided between the housing 26 and the outer globe 22 with an opening portion upside. The opening portion is hermetically sealed by a lid 28. The stored blood is packed separately and held in a retainer 29 provided with a handle 29a, and inserted in the inner globe 21 together with the retainer 29 where the blood is stored being immersed in liquefied nitrogen 20 of $-196°$ C. that is by far less than the recrystallization temperature of the ice.

In the Dewar bottle, the evaporation of the liquefied nitrogen 20 held in the inner globe 21 is prevented by maintaining the space 24 at a highly vacuum condition and restraining the heat transmission through this space. It, however, is difficult to fully prevent the evaporation, and it is necessary to replenish liquefied nitrogen by the degree of decrease, usually watching the residual quantity of the liquified nitrogen 20. The Dewar bottle has such disadvantages that not only this replenishing work is troublesome but also that equipments such as a tank for holding a great deal of liquefied nitrogen to be used for replenishing are required.

As a device for storing microbes, cells and the like in laboratories in the area of biotechnology, a very low temperaure freezer has been put to practical use wherein multiple freezing cycle is made use of, and this device can be used as a blood storing device. In this very low temperature freezer, vapor compression refrigerating machines having different refrigerants are used in multistage combination. Therefore, it has such disadvantages that the cost of equipment is high, the performance coefficient is low at a very low temperature and the running cost is high. In addition, because of the limit in the lowness in temperatures to be obtained the recovery rate of blood is low, in contrast with the Dewar bottle. Therefore, such a freezer is not suitable for a device for storing a great deal of blood.

SUMMARY OF THE INVENTION

The present invention has been made in order to solve the above-mentioned problems. The equipment for storing blood according to the present invention is such that a plurality of storing cases for storing blood are provided in a keeping-cool room which is kept at a low temperature, and that each storing case is refrigerated by a correspondingly-provided Stirling refrigerator.

An object of the present invention is to provide an equipment for storing blood wherein a very low temperature condition can be obtained at a low price.

Other object of the present invention is to provide an equipment for storing blood wherein the recovery rate of the stored blood is high.

Another object of the present invention is to provide an equipment for storing blood wherein it is possible to store a great deal of blood stably.

Another object of the present invention is to provide an equipment for storing blood which can save troublesomeness in the management of the equipment.

Another object of the present invention is to provide an equipment for storing blood capable of automatically performing taking blood in and out by providing a manipulating means which carries out putting blood in the storing case and taking out blood from the storing case.

Another object of the present invention is to provide an equipment for storing blood capable of performing taking blood in and out without the necessity of the operator's entering the keeping-cool room by providing an operating means which carries out remote controls of the above-mentioned manipulating means in addition to that manipulating means.

Yet another object of the present invention is to provide an equipment for storing blood capable of checking the increase in temperature in the keeping-cool room and the storing cases accompanying operations for storing blood by providing a means for refrigerating blood to some extent blood is put in the storing case.

The above and further objects and features of the invention will more fully be apparent from the following detailed description with accompanying drawings.

DESCRIPTION OF THE PREFERRED EMBODIMENTS

Figure 1:
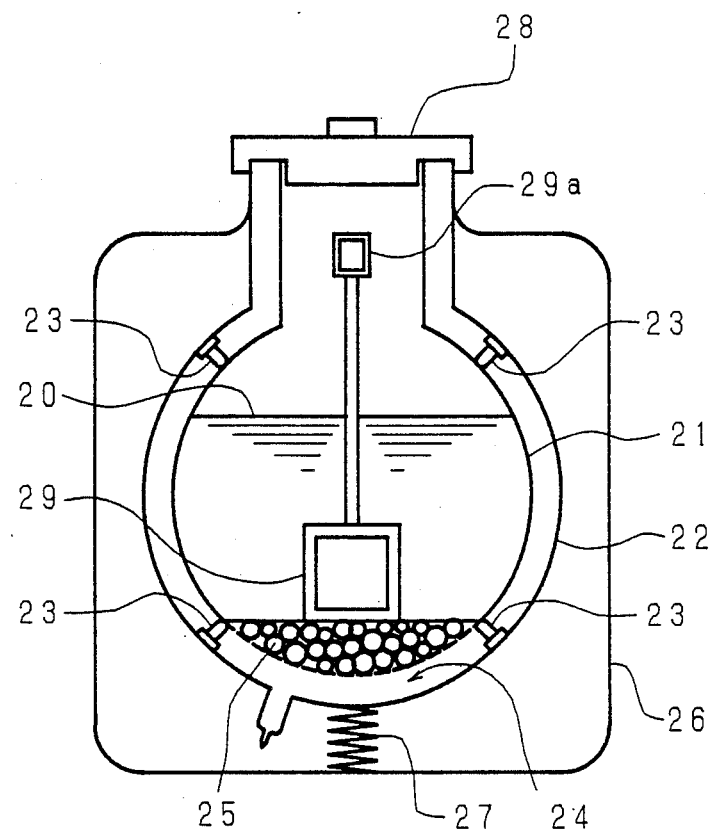
FIG. 1 is a sectional view of a Dewar bottle which is a conventional blood storing device.
Figure 2:
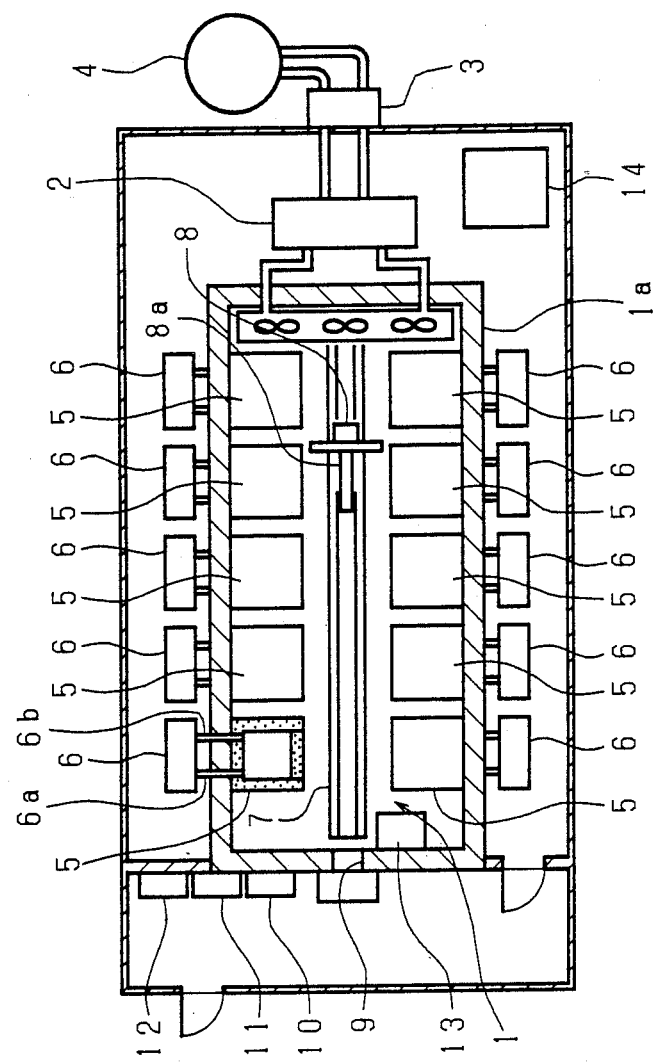
FIG. 2 is a plan view showing an entire structure of an equipment for storing blood according to the present invention.
Figure 3:
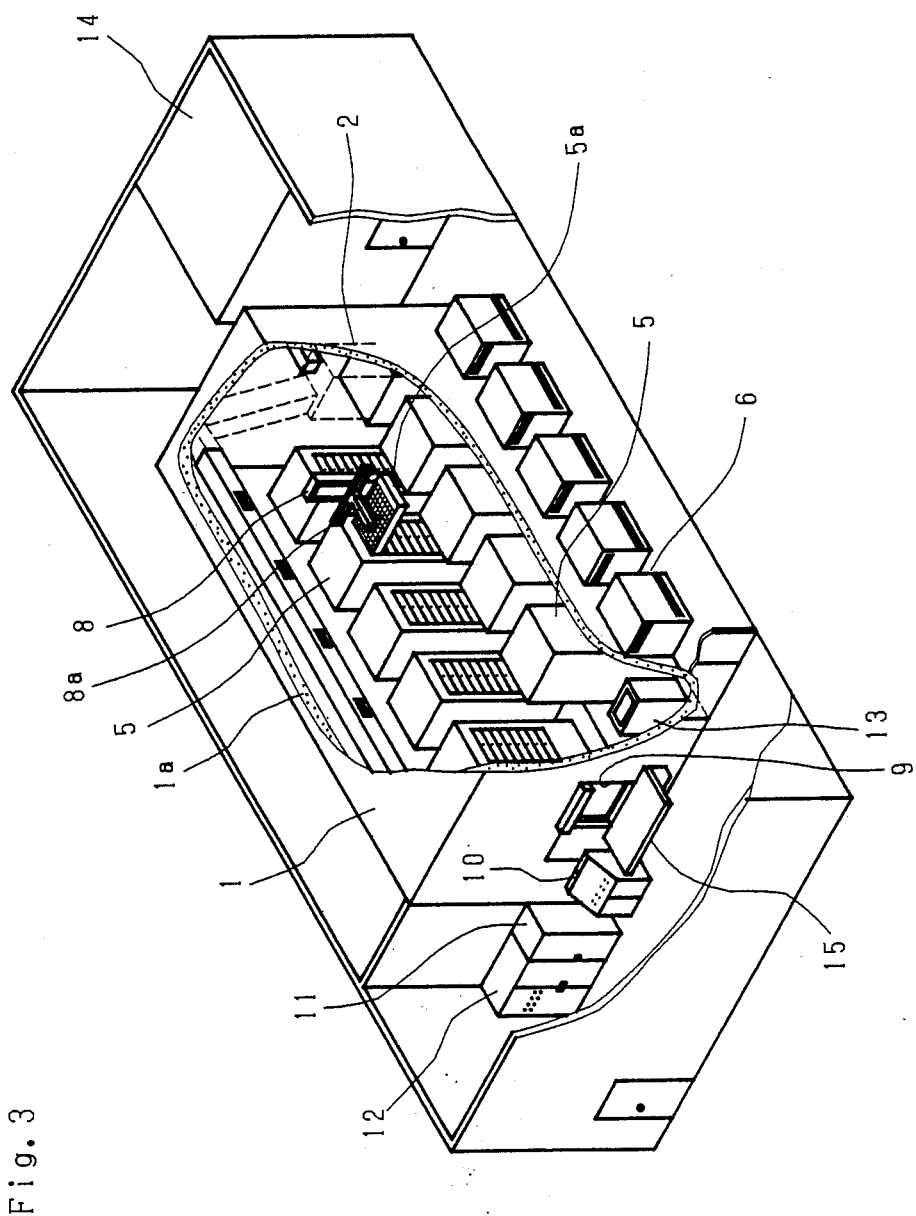
FIG. 3 is a perspective view showing the entire structure of the equipment for storing blood according to the present invention.

The present invention will be described hereinafter in detail with reference to the drawings showing embodiments thereof. FIG. 2 and FIG. 3 are a plan view and a perspective view respectively, showing the entire structure of an equipment for storing blood according to the present invention.

In the figures, numeral 1 denotes a keeping-cool room surrounded by an insulating wall 1a. The air in the keeping-cool room 1 is forced to circulate within a refrigerator 2 provided outside thereof, and the keeping-cool room 1 is kept at a low temperature condition by the operations of the refrigerator 2 and the insulation effect of the insulating wall 1a. As the temperature in the keeping-cool room 1, such a low temperature as obtainable under a high performance coefficient by a vapor compression refrigerating machine wherein a refrigerant for the room temperature is used will do, while a general vapor compression refrigerating machine can be used as the refrigerator 2. The refrigerator 2 is connected to a heat exchanger 3 and a cooling tower 4 installed in the open, and refrigerates the interior of the keeping-cool room 1, carrying out the well-known operations, that is, absorbing the retention heat of the circulating air from the keeping-cool room 1 upon the evaporation of the refrigerant, radiating this heat into the cooling water upon the condensation of the refrigerant in the heat exchanger 3, further radiating it in the open air in the cooling tower 4.

In the keeping-cool room 1 as constructed in this way, a plurality of storing cases 5 are provide in order to put stored blood within, for example, in a row lengthwise on both sides widthwise thereof. Each storing case 5 has a plurality of slide-out shelves 5a being multistage drawers vertically. Correspondingly to the address assigned to each slide-out shelf 5a, for example, the blood sorted out, for example, according to a blood type, a collected date, a donor's name and the like, is put in the slide-out shelf 5a. Each storing case 5 is connected to each of Stirling refrigerators 6 installed outside of the keeping-cool room 1, by means of respective circulating pipes 6a, 6b, and refrigerated to a very low temperature by the operations of the Stirling refrigerator 6 as will be described later.

Widthwise at the central portion of the keeping-cool room 1, a guide rail 7 is laid lengthwise substantially over the full length thereof, and a manipulator 8 is provided which moves along this rail 7. The manipulaor 8 has a carrier arm 8a capable of moving vertically within the range of the height of the storing case 5 and widthwise within a prescribed range. The manipulator 8 carries out taking out the stored blood which is put in a prescribed slide-out shelf 5a of a prescribed storing case 5 and bringing it out outside of the keeping-cool room 1 as well as bringing blood in the keeping-cool room 1 and putting it in a prescribed slide-out shelf 5a of a prescribed storing case 5, by the manipulator's travel along the guide rail 7 and the travel of the carrier arm 8a. Bringing-out blood outside of the keeping-cool room 1 and bringing-in blood inside of the keeping-cool room 1 are carried out through a bringing-in-and-out port 9 which is opened piercingly through the insulating wall 1a and faced an end portion of the guide rail 7 and a stage 15 attached to the insulating wall 1a. This port 9 is provided with a lid plate (not shown). This lid plate opens only when blood is brought out and brought in, and the port 9 is normally closed sealingly.

Outside the keeping-cool room 1, provided are an operational board 10 near the port 9 for operating the manipulator 8, a control unit 11 for not only carrying out drivingcontrol of the refrigerator 2 so as to keep the interior of the keeping-cool room 1 at a prescribed temperature but also carrying out driving-control of the Stirling refrigerators 6 so as to keep the interiors of the storing cases 5 at a prescribed temperature, a filing computer 12 for registering and filing the informations on the blood stored in each slide-out shelf 5a of a storing case 5. Numeral 13 is a program freezer to cool blood brought in the keeping-cool room 1 to a prescribed temperature and it is installed near the port 9 in the keeping-cool room 1. Numeral 14 is a private generator of electricity for the power compensation in a power failure and it is installed outside of the keepingcool room 1.

Each Stirling refrigerator 6 has a well-known arrangement wherein a very low temperature is realized, causing a refrigerant gas with a very low boiling point such as helium to suffer from a state-change, for example, and radiating outside in the isothermal compression process the absorbed heat in the isothermal expansion process, according to the reverse cycles of Stirling repeating the process of the isothermal compression, the isovolumetric cooling, the isothermal expansion and the isovolumetric heating in this sequence. Now the structure and the operation of each Stirling refrigerator 6 will be described briefly.

FIGS. 4–7 are sectional views showing schematically the principal parts of a Stirling refrigerator 6 for an explanation of the operation. The Stirling refrigerator 6 is constructed as such that an expansion piston 62 and a compression piston 63 are slidably fitted in a cylinder 61 which is capable of communicating longitudinally by a commnication path 60. Both pistons 62 and 63 are driven through a transmission mechanism (not shown) such as a crank mechanism to reciprocate vertically with the same cycle as will be mentioned later. Halfway in the communication path 60, provided are a cooler 64 which carries out a heat exchange between the cooling water, a heat acumulator 65 positioned above the cooler 64, and further a heat exchanger 66 having a plurality of fins and carrying out a heat exchange between the object to be cooled at the outside of the top of the cylinder 61.

Figure 4:
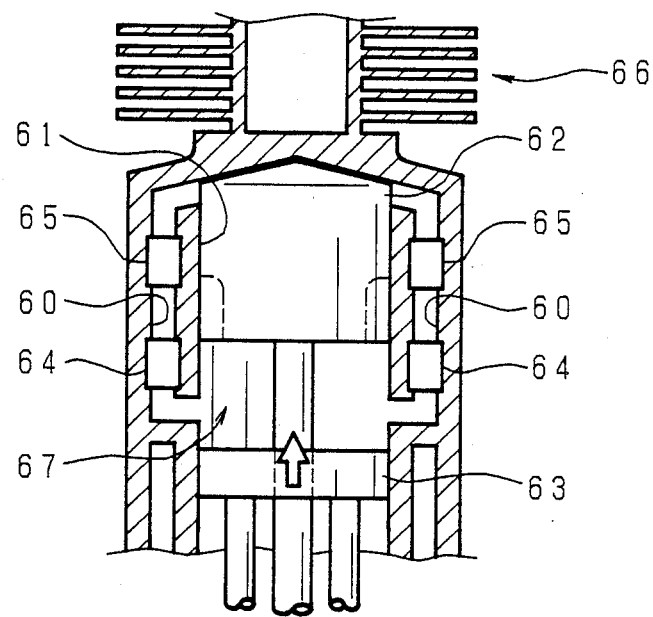
FIGS. 4–7 are sectional views for giving explanations of the operations of the Stirling refrigerator.

As shown in FIG. 4, the compression piston 63 moves upward as shown by a white arrow in the figure, at a state where the expansion piston 62 stands still at the top dead center thereof, and the refrigerant gas is compressed at a compression space 67 formed between the lower surface of the expansion piston 62 and the upper surface of the compression piston 63. This compression is carried out under a substantially isothermal state due to the radiation of the heat to the coolers 64. This process is the isothermal compression process.

Figure 5:
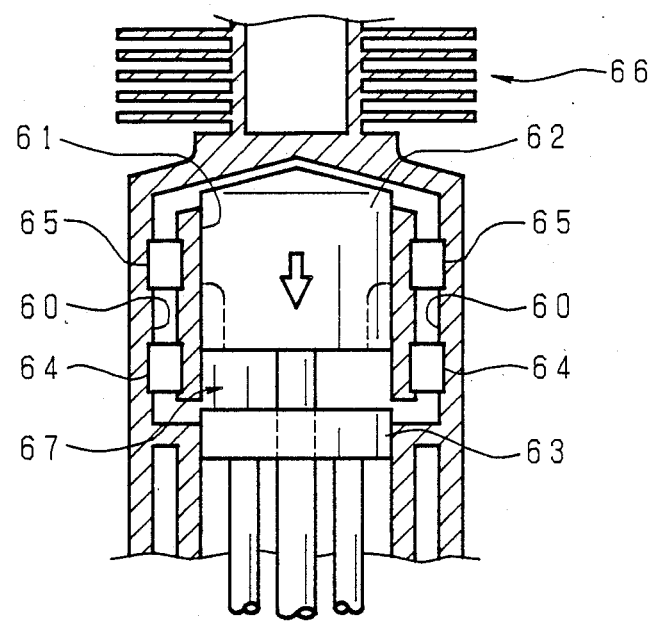

When the compression piston 63 reaches a prescribed position to stand still, the expansion piston 62 starts moving downward, as shown by a white arrow in FIG. 5. As a result, the volume of a expansion space 68 (see FIG. 6) formed above the expansion piston 62 increases, while that of the compression space 67 decreases. Consequently, the refrigerant gas in the compression space 67 is introduced into the expansion space 68 through the communication path 60 with its volume kept fixedly. At this time, the refrigerant gas is deprived of its retention heat by the heat accumulator 65 to be at a low temperature, while the heat accumulator 65 accumulates this heat. This process is the isovolumetric cooling process.

Figure 6:
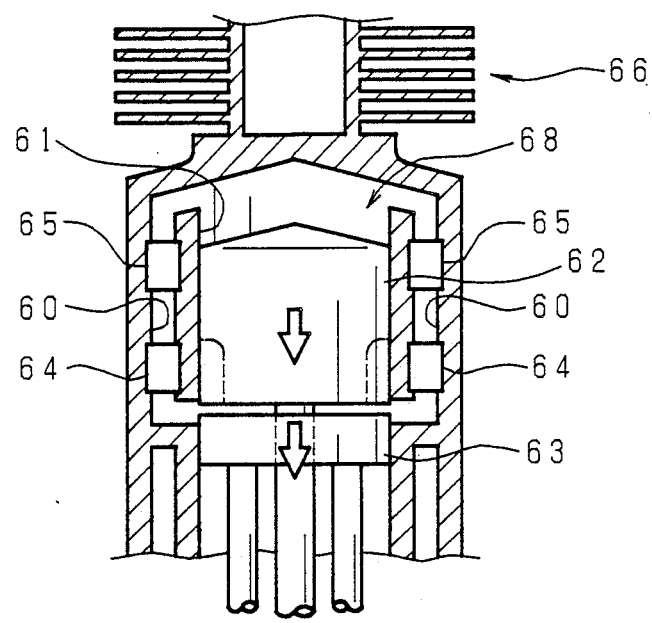

After the expansion piston 62 moves downward to a prescribed position, the compression piston 63 also starts moving downward, as shown by white arrows in FIG. 6. As a result, the volume in the expansion space 68 increases, and the refrigerant gas in the expansion space 68 expands. This expansion is carried out under an isothermal state where the retention heat of the object to be cooled which contacts the heat exchanger 66 is absorbed through the heat exchanger 66. This process is the isothermal cooling process. In the equipment for storing blood according to the present invention, a storing case 5 and a Stirling refrigerator are connected to each other by means of circulating pipes 6a and 6b, and the air in the storing case 5 is caused to circulate in contact to the heat exchanger 66, which results in that the retention heat of the air is absorbed in the refrigerant gas in the expansion space 68.

Figure 7:
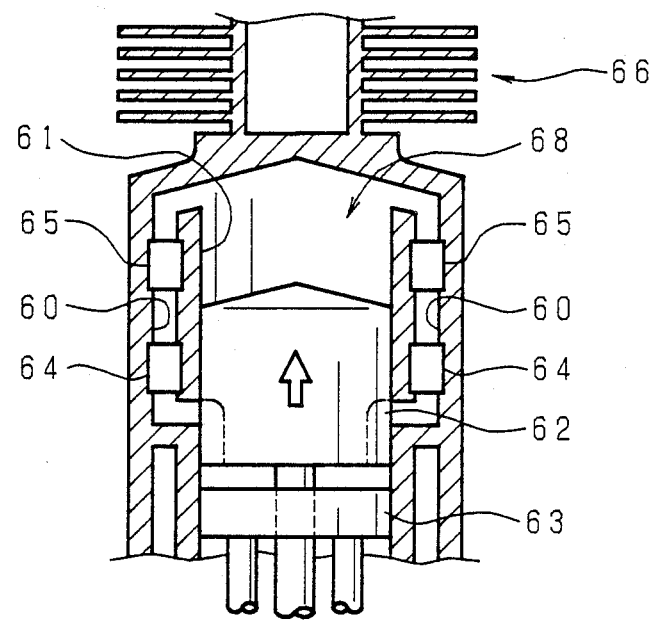

After both pistons 62 and 63 finish moving downward, the expansion piston 62 alone moves upward until it reaches the top dead center, as shown by a white arrow in FIG. 7. As a result, the volume of the expansion space 68 decreases, while that of the compression space 67 increases. Consequently, the refrigerant gas in the expansion space 68 is introduced into the compression spacer 67 through the communication path 60 with its volume kept fixedly. At this time, the refrigerant gas is heated due to the acumulated heat in the heat accumulator 65. This process is the isovolumetric heating process.

The Stirling refrigerator 6 repeats the operation of absorbing the retention heat of the air which contacts the heat exchanger 66, that is, the air in the storing case 5 in the refrigerant gas inthe isothermal expansion·process, and radiating this absorbed heat in the cooling water introduced into the cooler 64 in the isothermal compression process. Consequently, the interior of the storing case 5 is sequentially refrigerated until it reaches a very low temperature.

When blood is brought in the equipment for storing the blood having such a structure as mentioned above, a blood type, a collected date and a donor's name are first registered on the filing computer 12. Then the blood put in a prescribed vessel is placed on the stage 15, and the operational board 10 is operated. Following this, the manipulator 8 travels and its carrier arm 8a is projected from the port 9. The vessel is grasped by the carrier arm 8a and brought in the keeping-cool room 1. The blood brought in the keeping-cool room 1 is first introduced into the program freezer 13 by the operation of the carrier arm 8a and cooled in the program freezer 13 until it reaches the prescribed temperature. The cooled blood is taken out by the operation of the carrier arm 8a, carried to the front portion of a prescribed storing case 5 by the travel of the body of the manipulator 8, then it is raised to a position of the height of a prescribed slide-out shelf 5a of the storing case 5. Then the carrier arm 8a draws out the slide-out shelf 5a to put the blood in at a prescribed position in the slide-out shelf 5a, and further, carries out closing the slide-out shelf 5a to end the bringing-in operation of the blood. The position where the blood is put is registered on the filing computer 12 correspondingly to the information on the blood that has already been registered.

When stored blood which is put in a slide-out shelf 5a of a storing case 5 is brought out, the desired type of blood or the like is first inputted in the filing computer 12. Then the operational board 10 is operated. The filing computer 12 retrieves the position where the blood corresponding to the inputted content is put and sends a command to travel to the manipulator 8. In accordance with this command, the manipulator 8 travels to the front portion of the storing case 5 corresponding to the position where the blood is put, then draws out the slide-out shelf 5a by the operation of the carrier arm 8a, takes out the vessel where the desired blood is put from the slide-out shelf 5a, further closes the slide-out shelf 5a, then travels toward the port 9, then places this vessel on the stage 15 outside the keeping cool room 1, finally returns to a prescribed waiting position.

In the equipment for storing blood according to the present invention, each storing case 5 wherein blood is put is refrigerated by each Stirling refrigerator 6 with an excellent performance coefficient in a low temperature. Consequently, it is possible to realize a very low temperature less than $-135°$ C. that is the recrystallization temperature of the ice at a low cost. Moreover, as these storing cases 5 are provided in the keeping-cool room 1 kept at a low temperature, the load in the Stirling refrigerator 6 is small. In addition, in bringing in or out blood as mentioned above, a prescribed slide-out shelf 5a alone is drawn out, so that the increase in temperature generated in the storing case 5 is small, and the resulting increase in the load in the Stirling refrigerator 6 is small.

In this embodiment of the present invention, taking out stored blood from the storing case 5 and putting blood on the storing case 5 are automatically carried out by the operation of the manipulator 8. There, however, is another alternative that one operator putting on a heavy winter cloth enters the keeping-cool room 1 and he himself carries out taking-out and putting-in operation.

Also in this embodiment, a program freezer 13 is provided in the keeping-cool room 1 for cooling brought-in blood. But a Dewar bottle can be used instead. This Dewar bottle is used only for cooling brought-in blood and it is provided in the keeping-cool room 1 kept at a low temperature, so that the consumption of the liquefied nitrogen in the Dewar bottle is very small.

In FIGS. 4-7, an integrally formed type of Stirling refrigerator 6 is shown which has an expansion space 68 and a compression space 67 at the upper portion and the lower portion respectively of one cylinder 61. It, however, it needless to say that a separate type can also be used which has an expansion cylinder for an expansion piston 62 and a compression cylinder for a compression piston 63, as Stirling refrigerator 6.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within the meets and bounds of the claims, or equivalence of such meets and bounds thereof are therefore intended to be embraced by the claims.

What is claimed is:

1. An equipment for storing blood, comprising:
   a keeping-cool room kept at a low temperature,
   a plurality of storing cases for storing blood provided in said keeping-cool room, and
   Stirling refrigerators each of which is connected to each of said storing cases and refrigerates the interior of each of them to a very low temperature.

2. An equipment for storing blood as set forth in claim 1, wherein said keeping-cool room is refrigerated by a vapor compression refrigerating machine.

3. An equipment for storing blood as set forth in claim 1, further comprising a manipulating means for putting the blood in said storing cases and taking out the blood from said storing cases.

4. An equipment for storing blood as set forth in claim 3, further comprising an operating means being provided outside of said keeping-cool room, for operating said manipulating means.

5. An equipment for storing blood as set forth in claim 1, wherein blood is put in a vessel and said vessel is stored in said storing cases.

6. An equipment for storing blood as set forth in claim 5, further comprising a manipulating means having an arm portion for grasping said vessel, for manipulating the taking in and out of said vessel.

7. An equipment for storing blood as set forth in claim 1, further copmrising a filing means for filing the informations on the blood stored in said storing cases.

8. An equipment for storing blood as set forth in claim 7, wherein the informations on the stored blood include a blood type, a collected date and a donor's name.

9. An equipment for storing blood as set forth in claim 1, wherein said Stirling refrigerators refrigerate said storing cases in accordance with a change of the state of a helium gas.

10. An equipment for storing blood as set forth in claim 1, further comprising a cooling means for cooling the blood before storing the blood in said storing cases.

11. An equipment for storing blood as set forth in claim 1, wherein said very low temperature is $-135°$ C. or less.

* * * * *